(12) United States Patent
Hafezi et al.

(10) Patent No.: US 10,182,941 B2
(45) Date of Patent: Jan. 22, 2019

(54) APPARATUS FOR THE TREATMENT AND/OR PREVENTION OF CORNEAL DISEASES

(75) Inventors: Farhad Hafezi, Vesenaz (CH); Olivier Richoz, La Chaux-de-Fonds (CH)

(73) Assignee: Farhad Hafezi, Baar (CH)

(*) Notice: Subject to any disclaimer, the term of this patent is extended or adjusted under 35 U.S.C. 154(b) by 861 days.

(21) Appl. No.: 14/114,356

(22) PCT Filed: Apr. 23, 2012

(86) PCT No.: PCT/CH2012/000090
§ 371 (c)(1),
(2), (4) Date: Dec. 20, 2013

(87) PCT Pub. No.: WO2012/145853
PCT Pub. Date: Nov. 1, 2012

(65) Prior Publication Data
US 2014/0114232 A1 Apr. 24, 2014

Related U.S. Application Data

(60) Provisional application No. 61/480,443, filed on Apr. 29, 2011.

(51) Int. Cl.
*A61F 9/008* (2006.01)
*A61F 9/007* (2006.01)
(Continued)

(52) U.S. Cl.
CPC ............ *A61F 9/008* (2013.01); *A61F 9/0079* (2013.01); *A61N 5/06* (2013.01); *A61N 5/062* (2013.01);
(Continued)

(58) Field of Classification Search
CPC .................. A61F 9/0079; A61F 9/008; A61F 2009/00844; A61F 2009/00872;
(Continued)

(56) References Cited

U.S. PATENT DOCUMENTS 4,917,486 A * 4/1990 Raven ................. A61F 9/00821
351/221
5,295,989 A * 3/1994 Nakamura .............. A61F 9/008
606/10

(Continued)

FOREIGN PATENT DOCUMENTS

EP 1561440 8/2005
JP 2005-527493 9/2009
(Continued)

*Primary Examiner* — Kevin C Sirmons
*Assistant Examiner* — Tiffany Legette-Thompson
(74) *Attorney, Agent, or Firm* — Rankin, Hill & Clark LLP

(57) ABSTRACT

An apparatus for the treatment and/or prevention of corneal diseases includes an applicator head. The applicator head includes a radiation source capable of exciting a non-toxic chromophore. A control is operable to activate the radiation source to radiate, wherein at least one of the following two conditions is met: the applicator head includes a sensor capable of measuring a signal dependent on a position of the applicator head relative to the cornea; or, the applicator head is configured to be in physical contact with the cornea. The control is operable to activate the radiation source to radiate depending on a signal measured by the sensor or to activate the radiation source when the applicator head touches the cornea, respectively.

19 Claims, 3 Drawing Sheets

(51) Int. Cl.
   *A61N 5/06* (2006.01)
   *A61F 9/009* (2006.01)

(52) U.S. Cl.
   CPC ..... *A61F 9/009* (2013.01); *A61F 2009/00872* (2013.01); *A61F 2009/00893* (2013.01); *A61N 2005/0643* (2013.01); *A61N 2005/0651* (2013.01); *A61N 2005/0661* (2013.01)

(58) Field of Classification Search
   CPC .. A61F 9/009; A61F 2009/00893; A61F 9/06; A61F 9/062; A61F 2009/00885; A61N 5/062; A61N 5/06; A61N 2005/0661; A61N 2005/0651; A61N 2005/0643
   USPC .................................................. 604/20, 501
   See application file for complete search history.

(56) References Cited

U.S. PATENT DOCUMENTS

| | | |
|---|---|---|
| 6,120,460 A | 9/2000 | Abreu |
| 2001/0031960 A1* | 10/2001 | Kliewer ............ A61F 9/00806 606/5 |
| 2003/0095234 A1* | 5/2003 | Heacock ............ A61B 3/125 351/219 |
| 2004/0019032 A1* | 1/2004 | North ............ A61K 41/0071 514/185 |
| 2006/0084951 A1 | 4/2006 | Heacock |
| 2006/0155179 A1* | 7/2006 | Muller ............ A61B 5/14532 600/318 |
| 2007/0185553 A1* | 8/2007 | Kennedy ............ A61N 5/0616 607/100 |
| 2007/0225778 A1* | 9/2007 | Heacock ............ A61F 9/0079 607/88 |
| 2008/0144028 A1* | 6/2008 | Gruler ............ G01N 21/645 356/317 |
| 2008/0208177 A1* | 8/2008 | Mrochen ............ A61F 9/008 606/5 |
| 2008/0218696 A1 | 9/2008 | Mir |
| 2009/0024112 A1* | 1/2009 | Edwards ............ A61M 5/19 604/890.1 |
| 2009/0192437 A1 | 7/2009 | Soltz et al. |
| 2010/0057060 A1 | 3/2010 | Herekar |
| 2010/0069894 A1 | 3/2010 | Mrochen et al. |
| 2010/0210996 A1* | 8/2010 | Peyman ............ A61F 7/007 604/20 |

FOREIGN PATENT DOCUMENTS

| | | |
|---|---|---|
| WO | 03/061696 | 7/2003 |
| WO | 2009/042159 | 4/2009 |

* cited by examiner

APPARATUS FOR THE TREATMENT AND/OR PREVENTION OF CORNEAL DISEASES

BACKGROUND OF THE INVENTION

Field of the Invention

The present invention generally relates to treating and preventing diseases of the cornea and, more particularly, toward apparatuses and methods for releasing free radicals and/or for causing a cross-linking of the collagen by photoactivating a therapeutic agent.

Description of Related Art

Corneal Collagen Crosslinking (CXL) is a treatment of the cornea in which a chromophore, for example Riboflavin eye drops, is applied, and then Ultraviolet (UV) radiation impinges on the cornea to increase collagen cross-links. Currently, the CXL treatment is being clinically tested to determine if it can be effectively used to treat primary (keratoconus) and secondary (iatrogenic keratectasia) ectatic diseases of the cornea and infectious (bacterial, viral, fungal and parasitical) and non-infectious corneal melting. Specifically, the combined application of Riboflavin and UV exposure causes a cross-linking of the collagen increasing the mechanical strength of the cornea. Also, it may eliminate infectious microbial, fungal and parasite agents that cause these infections presumably by generating free radicals that disrupt. Further, the combined application of Riboflavin and UV exposure increases the stromal resistance against enzymatic digestion through steric hindrance. Similarly, the changed physiology caused by the cross-linking may prevent organisms from getting into deeper tissue portions Application of UV radiation to human tissue is potentially harmful, since over-exposure may damage ocular tissues.

In WO 2009/042159, a wearable photoactivator for ocular therapeutic applications is disclosed. The device comprises a wearable frame to which a light source housing is attached. In embodiments, different lenses of different sizes can be brought into position, and an infrared source-phototransistor pair can be used to detect which of the lens sizes is in position. The radiation source controlling current can depend on the phototransistor signal. The radiation source may further comprise a rear facet photodetector or similar to provide constant power output.

UV radiation, if applied with too strong intensities or under wrong circumstances, can have a damaging effect. A disadvantage of the photoactivator of WO 2009/042159 is that the correct operation depends on the settings the ophthalmologist chooses. Therefore, a photoactivator as taught in WO 2009/042159 can only be used by specialized and well trained ophthalmologists.

SUMMARY OF THE INVENTION

It is an object of the present invention to provide an improved apparatus for the treatment and/or prevention of corneal diseases. It is a further object to provide an apparatus for the treatment and/or prevention of corneal diseases with particular emphasis on infectious and non-infectious corneal melting. It is a further object to provide an apparatus that is easy to handle so that general ophthalmologists may use it.

In accordance with an aspect of the invention, an apparatus for the treatment and/or prevention of corneal diseases includes:

an applicator head, the applicator head comprising a radiation source capable of exciting a non-toxic substance; and a control operable to activate the radiation source to radiate;

wherein at least one of the following two conditions is met:

the applicator head comprises a first sensor capable of measuring a signal dependent on a position of the applicator head relative to the cornea;

the applicator head is configured to be in physical contact with the cornea;

and wherein the control is operable to activate the radiation source to radiate depending on a signal measured by the sensor or to activate the radiation source when the applicator head touches the cornea, respectively.

In all aspects of the invention, the control or parts thereof may be integrated in the applicator head, the control may comprise parts integrated in the applicator head and a separate control unit (or control units) in communication with the applicator head or the control may be integrated in a separate unit/separate units.

The non-toxic substance may be a photoactivatable therapeutic agent, i.e. a substance that can, through irradiation, be brought into a state in which it has some property it would not have if it was not irradiated and that enables it to help in the treatment and/or prevention. The portion of the substance that responds to the radiation is called "chromophore". In many, cases, when irradiated, such a chromophore emits radiation at a different, longer wavelength (fluorescence). An example of a non-toxic substance is riboflavin.

The radiation source is generally a source of electromagnetic radiation, especially UV, visible or infrared light, especially radiation with a specific wavelength or wavelength range that depends on the absorption spectrum of the used chromophore. Especially, the emission wavelength may be within the range between 280 nm and 1500 nm or, for example, specific wavelength between 280 and 1300 nm, or within the range between 300 nm and 1400 nm, in examples between 300 nm and 800 nm, or for example, between 300 nm and 500 nm. The radiation source may comprise a light emitting element, such as an LED, integrated in the applicator head itself Alternatively, the radiation source may be constituted by endings of fiber optic cables connected to at least one light emitting element arranged elsewhere, for example in the control. In such an embodiment, the radiation source comprises at least one fiber optic cable that connects a distal portion of the applicator head with a radiation generating element placed outside of the applicator head—or optionally also in the applicator head.

A 'fiber optic cable' in the present context comprises optical fiber and optionally has a jacket or other outer protection to protect the fiber itself If radiation with a certain spectral width is to be transmitted, the fiber(s) used is/are often multimode fibers.

In all aspects, the first sensor may be a sensor capable of measuring the saturation of the cornea with the photoactivatable therapeutic agent, for example by measuring the fluorescence caused by the chromophore when the radiation generated by the radiation source is incident and the applicator head is close enough.

In all aspects, the applicator head may be configured to fit the standard holders for Goldmann applanation tonometry devices of the currently used slit lamps.

In accordance with another aspect, the apparatus for the treatment and/or prevention of corneal diseases comprises an applicator head with a radiation source capable of exciting a non-toxic photoactivatable therapeutic agent; and a control operable to activate the radiation source to radiate; wherein the control is configured to not activate the radiation source when no proximity and/or fluorescence feedback is sensed, which feedback indicates that the applicator head is near the cornea and/or that the photoactivatable therapeutic agent is present in sufficient concentration.

This configuration may be achieved by the above-mentioned device, i.e. the applicator head comprising a first sensor capable of measuring a signal dependent on a position of the applicator head relative to the cornea and/or the saturation of the cornea with a non-toxic photoactivatable therapeutic agent, or the applicator head being configured to be in physical contact with the cornea.

The approach according to aspects of the invention brings about the advantage that the apparatus is easy to handle and that mishandling is effectively prevented. Therefore, also general ophthalmologists can safely use the apparatus. This is of particular interest in countries with high corneal infection rates but with only very few highly specialized ophthalmologists (corneal specialists) available.

The presence of a sensor sensing a fluorescent signal may have a double function. It firstly ensures that the photoactivatable therapeutic agent is present in sufficient concentration. This may, dependent on the application case, be important to make sure that the radiation is sufficiently absorbed. This ensures the proper cross-linking to occur, but also ensures that deeper ocular structures are not damaged. It also prevents the general ophthalmologist from starting the irradiation treatment without proper saturation of the cornea with the photoactivatable therapeutic agent. Secondly, it ensures that the applicator head is properly placed, since if the sensor is too far way from the place where the fluorescent substance is the signal will be too weak.

The control may in an embodiment be programmed to allow the ophthalmologist to switch the radiation source on. If after switching on the sensed signal is below a threshold (the "sensed signal" may optionally be a sum or an average of the sensor signal over time or other value derived from the sensor signal), the radiation source is switched off, and a visual and/or acoustic signal, for example, is output to the ophthalmologist, and/or a computer connected to the control indicates the condition. If the sensed signal is above the threshold, the radiation source may be activated to radiate during a pre-determined time (or, more generally, is subject to a pre-determined intensity profile), whereafter the radiation source is automatically switched off. During irradiation, the sensor may optionally remain active and capable of switching the radiation source off.

In embodiments that comprise a proximity sensor in addition to the fluorescence sensor or instead of a fluorescence sensor, the detection of proximity by the proximity sensor may be a required condition for the radiation source to be activatable. If both, a first proximity sensor and a second fluorescence sensor are present, the control optionally may be configured to activate the radiation source only if proximity is detected and certain conditions for the fluorescent radiation are met. Especially, in an example, the radiation may only be activated or continue if all of the following conditions are met.

the proximity detector detects proximity (i.e. the applicator head is at a distance within a pre-determined distance range from the cornea)

the fluorescence signal is, the light source being switched on, above a certain threshold level, the accumulated dosage, calculated from the accumulated fluorescence signal and/or from the accumulated radiation power, does not exceed a certain maximum.

A threshold intensity for the signal obtained from the sensor sensing a fluorescent signal may be pre-set or may be programmable.

Instead of this on/off-operation, a more sophisticated relation between the sensed signal and the output is possible; for example the radiation output may be controlled to maintain the fluorescence signal at a certain desired level as long as the required radiation power does not exceed a certain level, etc.

The apparatus may further provide for the possibility to generate and store a protocol of the process. Logged data may comprise the sensed signal, the radiation source current (or other radiation source operation data) and/or the radiation time, etc. The data may be continuously, in real time, output from the control to an external device (such as a computer connected to a control) where it is logged, or may be stored in an internal memory and displayed and/or relayed at a later, desired time.

As mentioned, instead of being a detector of fluorescent radiation (for example photodiode), the first sensor/proximity sensor may also be another kind of sensor, for example a sensor sensing the physical contact to the cornea or an optical (for example IR) or ultrasound-based or capacitive or other distance measuring sensor. Sensors of this kind are known in the art and may rely on different physical principles.

Generally, the first sensor or an additional fluorescence sensor may comprise an active, electrically powered sensing element placed within the applicator head or may alternatively comprise an optical fiber or an electrode that connects to an active element outside of the applicator head, for example in the control unit. Especially, intrinsic or extrinsic fiber optic sensors may be used as an option for any one of the sensing functionalities discussed in the present text.

In addition or as a further alternative, the applicator head may also be equipped for the ophthalmologist to determine, by visual inspection, whether the applicator head is in contact with the cornea and to manually activate the control. The ophthalmologist is used to doing so for Goldmann applanation tonometry, and a mechanism corresponding to the one of a standard tonometer may be used in an apparatus according to the claimed invention.

Especially in embodiments where the first sensor is based on another kind of principle than detecting fluorescent radiation, or where the applicator head is configured to be in physical contact with the cornea, the system may further comprise a second sensor that measures the fluorescent radiation. In this, the second sensor may be sense the dosage of radiation incident on the eye.

The apparatus—for example the control itself or a software running on a computer communicatively connected to the control—may be configured to evaluate an accumulated dosage by integration of the appropriately processed sensor signal of the fluorescent sensor (i.e. first and/or second sensor).

The apparatus may especially be programmed to ensure that the dosage is accumulative; if the treatment is interrupted, the apparatus will remember the accumulated exposure and continue the treatment to complete a cycle. In this, as well as in other embodiments, the dosimeter may in addition or as an alternative comprise a measured or calculated value for the dosage of primary radiation incident from the light source on the eye. Such a measurement may for example comprise measuring the intensity a portion of the radiation generated by the light emitting element and directed, by fiber optics or other means, onto an intensity detector.

The combination of a first sensor that measures proximity/distance or physical contact with the cornea on the one hand and of a second sensor measuring fluorescence on the other hand may be especially advantageous because due to the independent distance information, the signal sensed by the fluorescence sensor is only dependent on the one parameter (fluorescence generated under the impact of the incident radiation) and thus suited for serving a precise dosimeter.

In embodiments where the proximity of the cornea is sensed independent of the fluorescence, the control may be programmed to not switch on the radiation source unless the proximity has been/is detected.

Conditions treated by an apparatus according to aspects of the invention may comprise infectious diseases of the cornea, such as infectious and non-infectious corneal melting, as well as diseases like keratoconus, iatrogenic keratectasia after refractive laser surgery, and Fuchs' corneal dystrophy, etc.

Suitable photoactivatable therapeutic agents include riboflavin in addition to other substances. A small list of phototherapeutic agents can for example be found in the above-mentioned reference WO 2009/042159.

The radiation source may comprise a single LED or a plurality of LEDs, especially radiation in the UV or visible part of the electromagnetic spectrum, especially emitting UVA radiation, especially with wavelengths larger than 300 nm, especially around 365 nm if the phototherapeutic agent is riboflavin.

The power of the radiation source may for example, be between 0.05 mW and 25 mW, or further between 1 mW and 10 mW for an irradiance of between 5 mW/cm$^2$ and 50 mW/cm$^2$, especially the irradiance may be between 10 mW/cm$^2$ and 30 mW/cm$^2$.

A distal end surface portion (at least a portion of which, in embodiments, comes into contact with the cornea) may have an overall surface area substantially smaller than the surface of the cornea, for example a surface area of between 3 mm$^2$ and 100 mm$^2$, for example it may have a diameter around 7 mm. The portion that comes into contact with the cornea may be substantially smaller then the overall area of the distal end surface portion.

The outer shape of the applicator head (or of a housing thereof) may have a portion corresponding to the shape of a standardized probe for which multifunctional equipment of the ophthalmologist has a mount. Especially, the applicator head housing may have a proximal cylindrical portion that can be introduced in mount of a standard Goldmann applanation tonometer as available from providers like Haag Streit, Kowa, Bon, Zeiss, Topcon, and others, for example of a prevalent slit lamp.

The applicator head may be available separate from the control. Especially, it may be a consumable, one-time use product provided in a sterile package. Because of semiconductor based components it may comprise (LED, sensor parts) it may be not sterilizable. Alternatively to being a one-time use product, the applicator head may comprise an exchangeable, transparent (for UVA radiation and for the fluorescent radiation if any) outer cover (or 'single use tip') which is shaped to partially encase the applicant head housing and is sterilizable and/or can be replaced after every use.

Such an exchangeable outer cover may optionally comprise an optical lens and/or at least one other feature that influences the radiation incident on the cornea and/or radiation coming from the cornea.

An exchangeable outer cover—if configured to be a single-use cover —may comprise a security feature that ensures one-time use. For example, the outer cover may have a barcode or machine-readable number or magnetic code or a unique pattern that may be identified with the built-in camera or other sign imprinted on it that uniquely identifies every single cover and thereby serves as security feature. The control may then be programmed to store the read information (sign) in memory and to refuse activation if an already-used outer cover is used. Such a barcode or number or other sign may for example be printed on the periphery of the cover so that there is no interference with radiation.

In addition or as an alternative to such a readable sign, the single-use tip may comprise a fuse feature, for example a structure that is irreversibly destroyed by an electric pulse at the end of the treatment.

In addition or as yet another alternative, the outer cover may be equipped for being used several times, and for being sterilized between subsequent uses. In such a case, a security feature may be configured to appear only after sterilization, for example caused by heat impact during sterilization, and to disappear after a certain exposure to air.

In addition or as yet another alternative, the single-use tip may be such as to be broken when removed from the applicator head. This may, for example, be combined with a capability of the applicator head to sense the removal of the outer cover. The apparatus may then be programmed to demand removal and exchange of the outer cover after a full treatment has been finished and before a new treatment can start. Other possibilities of ensuring single-use may be envisaged.

If the control is separate from the applicator head, then a control unit of an apparatus for the treatment and/or prevention of corneal diseases comprises an interface to an applicator head with a radiation source and with a sensor capable of measuring a signal dependent on a position of the applicator head relative to the cornea, the control unit being programmed to activate the radiation source only when a signal received from the sensor indicates that the applicator head is near enough to the cornea and/or indicates that the a sufficient amount of a chromophore is present on and/or in the cornea.

In this, the control unit may be or comprise a specifically adapted hardware that optionally has an interface for a computer, or alternatively may be constituted by a generic device—such as a computer, potentially with an additional generic interface device—programmed for the task.

A further optional feature of the apparatus is a camera integrated in the applicator head. The camera may be used to visualize the part of the cornea that is to be treated for the ophthalmologist. It may serve to obtain proper alignment, to monitor the cornea during treatment and/or to capture images and/or videos of the treatment for documentation purposes. In addition or as an alternative, it may optionally serve as the first sensor. For example, the camera may visualize the overlap of two different light spots on the cornea, and for a correct distance the overlap pattern then corresponds to a pre-defined image. It is further not excluded that the camera (having a spectral sensitivity) is also used to measure the fluorescence of emitted light. The camera may also be used to ensure the single use of the tip, as mentioned above.

A kit of parts may comprise, in addition to the applicator head, at least one dose of the photoactivatable therapeutic agent. The photoactivatable therapeutic agent and the emission spectrum of the radiation source may be adapted to each other so that an absorption maximum of the photoactivatable therapeutic agent's chromophore about coincides with the emission wavelength of the radiation source.

A method of treating and/or preventing a corneal disease may comprise the steps of:

applying a therapeutic amount of a photoactive therapeutic agent (in many embodiments in solution) to the cornea;

providing an apparatus with an applicator head, the applicator head comprising a radiation source capable of exciting a chromophore of the photoactive therapeutic agent, with or without prior abrasion of the corneal epithelium, depending on the ability of the solution to penetrate intact corneal epithelium;

positioning the applicator head near the cornea;

checking whether at least one of the following two conditions is met:

the applicator head is in physical contact with the cornea;

a sensor of the applicator head measures a signal that indicates that the applicator head is sufficiently close to the cornea and/or a sufficient amount of the chromophore is present on and/or in the cornea;

in case the at least one condition is met, irradiating the cornea by the radiation source and thereby activating the therapeutic agent.

The method may comprise the further step of stopping the treatment as soon as the distance between the applicator head and the cornea changes (patient's head movements) and/or an insufficient amount of the chromophore is present on and/or in the cornea.

In an example, the phototherapeutic agent is chosen to be riboflavin. In a first step, an abrasion of the corneal epithelium is performed or not, depending on the specific composition of the 0.1% riboflavin solution and its ability to pass an intact corneal epithelium. Then, the 0.1% concentration riboflavin solution is applied to the cornea for 30 minutes until the cornea is saturated. Thereafter, the cornea is subject to 365 nm radiation generated by an applicator head of the above described kind with a distal end face having a diameter of 7 mm. The applicator head comprises a 2×1 array of SMD LEDs of 3×2 mm (UVLED365-SMD by Roither Laser Technik, Vienna, Austria) each, so that the total area of the matrix is 3×4 mm. The LEDs are arranged at the distal end face without any additional lenses between the LEDs and the cornea. The total radiation power is chosen to be 3 mW (current: 20 mA), and the radiation is applied for 30 minutes. The penetration depth of the UVA radiation into the cornea is estimated to be between 300 and 330 μm. As the photodiode, a EPD-470-1/0.9 385-565 nm 0.62 mm$^2$ SMD GaP is used. Alternatively, the photodiode is chosen to be EPD-470-0-1.4 420-520 1.79 mm$^2$ GaP. As yet another alternative, a photodiode with an UV and blue filter may be used.

In an alternative example, same parameters are chosen, except that the radiation power is 10 mW and the duration of the application of the radiation is 3 to 5 minutes. Similar results are achieved.

Yet other embodiments are based on other phototherapeutic agents than riboflavin. Depending on the phototherapeutic agent, the spectrum of the radiation source is adapted. The output radiation can be ultraviolet, visible or near infrared, depending on the agent.

In an example, the other agent use is ofloxacin, for example in a concentration of 0.3 mg/ml (¹/₁₀ dilution of 3 mg/ml). The agent may be applied by cuvette, such as a 1 mm cuvette. The absorption spectrum has an edge at a wavelength of 350 nm with of between 90% and 100% below 335 nm in the UVA region of the electromagnetic spectrum.

BRIEF DESCRIPTION OF THE DRAWINGS

In the following, ways to carry out the invention and embodiments are described referring to drawings. The drawings are schematical. In the drawings, same reference numerals refer to same or analogous elements. The drawings show.

DESCRIPTION OF THE PREFERRED EMBODIMENTS

Figure 1:
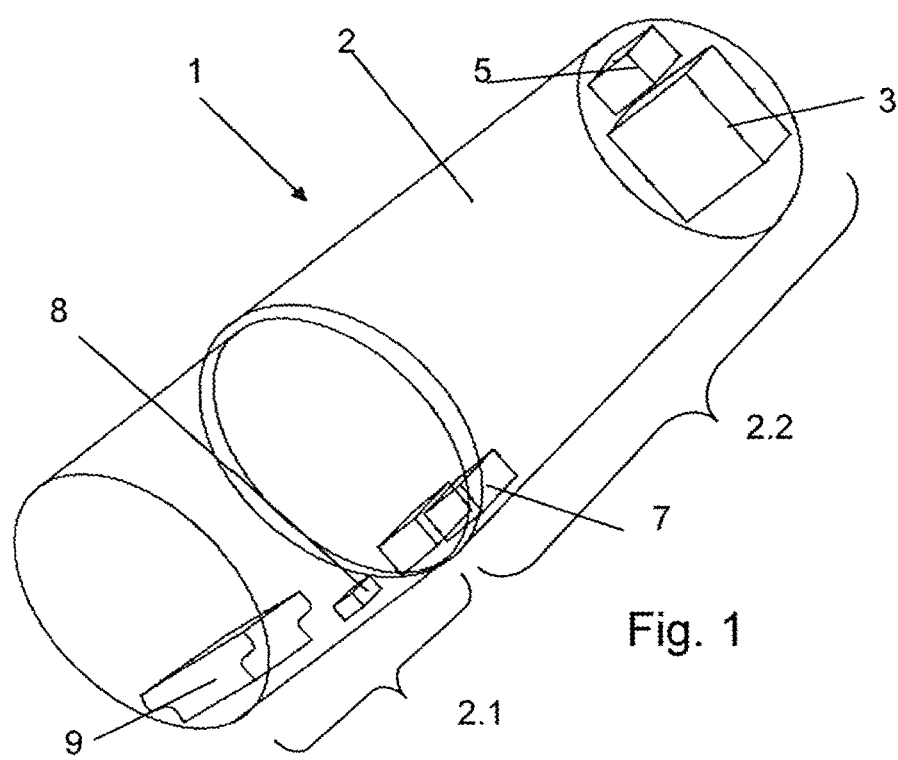
FIG. 1 a view of an applicator head.

In FIG. 1 a rear view (view from the proximal side) of the applicator head 1 is shown. For better visibility, the housing of the applicator head is shown transparent in the drawings, although in reality transparency is an optional, but not required property of the housing.

In the present description, the terms "proximal" and "distal" are used as seen from the ophthalmologist's point of view, i.e. "distal" is the portion closer to the eye/the cornea of the person to be treated and away from the side from which the ophthalmologist accesses the eye, whereas "proximal" is "closer to the ophthalmologist/further away from the eye of the person to be treated". In FIG.1, the proximal side is on the bottom left side of the applicator head and the distal side is on the upper right side of the applicator head.

The applicator head housing 2 has a proximal cylindrical portion 2.1 and a distal portion 2.2 that in the depicted configuration has a larger external diameter than the proximal portion 2.1. At the distal end face, at least one UVA LED 3 is arranged so that radiation generated by the LED 3 is radiated towards a distal side. Depending on the chosen configuration, a single LED or an arrangement, for example a matrix-like arrangement, of LEDs can be present. In an embodiment, the UVA LEDs comprise a 2×1-Matrix of two LEDs arranged next to one another, each having a 3×2 mm distally facing surface each, amounting to a total of a 3×4 mm radiating surface. The total radiating power in this embodiment is 3 mW, thus the irradiance is approximately 15 mW/cm$^2$. In the depicted embodiment, the applicator head does not have any lenses influencing the radiation radiated distally away from the UVA LEDs. This feature (no lenses between the LED(s) and the cornea) is an optional feature of any embodiment of the invention, except, of course, of the embodiments that are specifically designed with a lens or a plurality of lenses for example to homogenize the radiation power. Especially, in alternative embodiments, the applicator head may have a Koehler illumination.

In addition to the LED(s), the distal end face of the applicator head comprises a sensor 5 for sensing a signal that depends on the proximity of the cornea. More in concrete, the sensor 5 is a photodiode the sensitivity of which is in the wavelength region of fluorescent radiation radiated back by the cornea when the cornea is impregnated with the chromophore and the UV radiation generated by the LED(s) impinges. In accordance with an often advantageous feature, the sensor is chosen to be insensitive to primary radiation, i.e. to the radiation of the spectral composition that is generated by the LED(s).

In accordance with an embodiment, the LED(s) is/are chosen to have an emission wavelength of 365 nm (i.e. a spectral composition with an emission peak near 365 nm), while the chromophore is Riboflavin. The sensor then in an embodiment comprises a photodiode with a sensitivity for visible light (especially green and yellow light) with a sensitivity between 420 and 550 nm and with very small UV sensitivity. In an example, the sensor comprises a GaP photodiode.

The applicator head 1 in the depicted embodiment further comprises optional control lights 7 for treatment control (for example to show the ophthalmologist whether the UVA LEDs are on or off). An optional fuse 8 may have the function of a classical fuse (i.e. ensuring that the diode(s) and or potential electronics is/are not subject to too high voltages/currents). Alternatively, or in addition, the fuse 8 may be configured to interrupt the power line to the UV LED(s) after treatment to ensure that the applicator head is used once only. This feature may be advantageous in embodiments that do not comprise a sterile consumable distal outer cover and in which therefore the applicator head must only be used once.

As an alternative to being a one-time use device only, the applicator head may also comprise an exchangeable outer cover that can be replaced after every use.

At the proximal end, the applicator head comprises an interface to an external control unit and/or a computer, for example a mini USB connector 9. The connector here is placed in a way that does not hinder the ophthalmologist to have good visual control of the placement of the applicator head on the cornea.

In the interior of the applicator head, further components such as electronic equipment and/or wiring (not shown in the figures) may be arranged.

Figure 2:
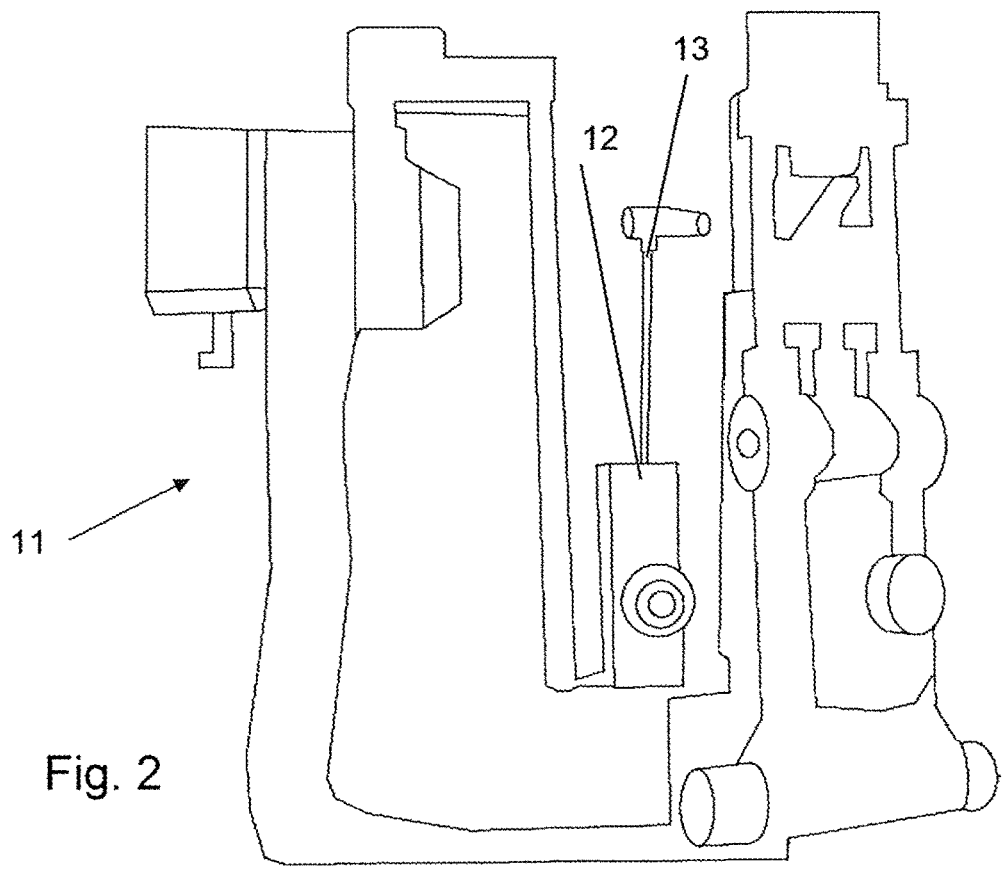
FIG. 2 a view of a slit lamp with an applanation tonometer in the mount of which an applicator head of an apparatus according to the present invention is introduced.
Figure 3:
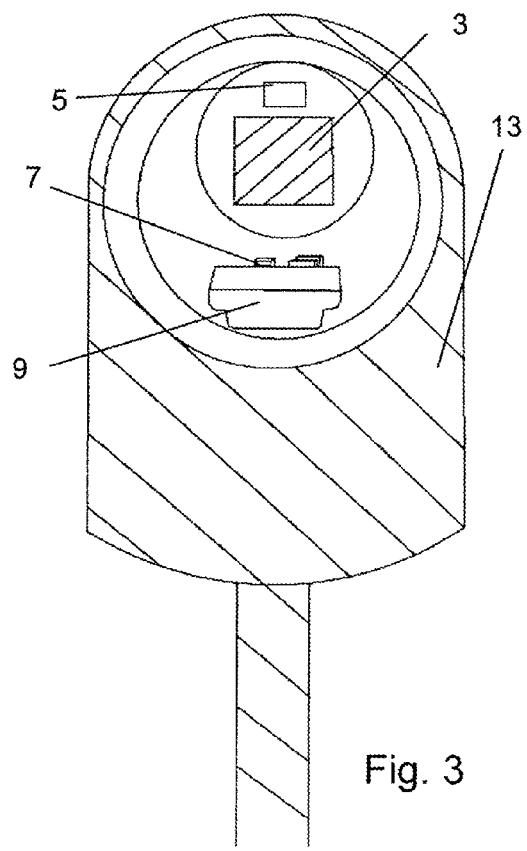
FIG. 3 a view of a tonometer mount with an applicator head.

The proximal, cylindrical portion 2.1 of the housing 2 is adapted for introduction into a mount of a standard Goldmann applanation tonometer, as illustrated in FIGS. 2-3. FIG. 2 depicts a commercially available slit lamp 11 of the kind that belongs to the standard equipment of every ophthalmologist. The slit lamp 11 comprises a Goldmann applanation tonometer 12. The tonometer 12 comprises a mount 13 for a sensing head. In accordance with embodiments of the present invention, the Goldmann applanation tonometer is, for the treatment, replaced by an applicator head of an apparatus according to the invention.

FIG. 3 shows a front view of the applicator head introduced into the mount 13. Again, for better visibility the housing of the applicator head is shown transparent. In the depicted configuration, the position of the LED(s) 3 and the sensor on the one hand and of the connector 9 and the control lights 7 on the other hand are, when seen along the proximodistal axis, offset with respect to each other. If the housing is at least partially transparent, similar to the standard heads actually used for Goldmann applanation tonometry, this arrangement makes possible that the ophthalmologist has a visual control and can make sure that the applicator head makes contact with the cornea—like she/he is used to checking from a Goldmann applanation tonometer head.

Figure 4:
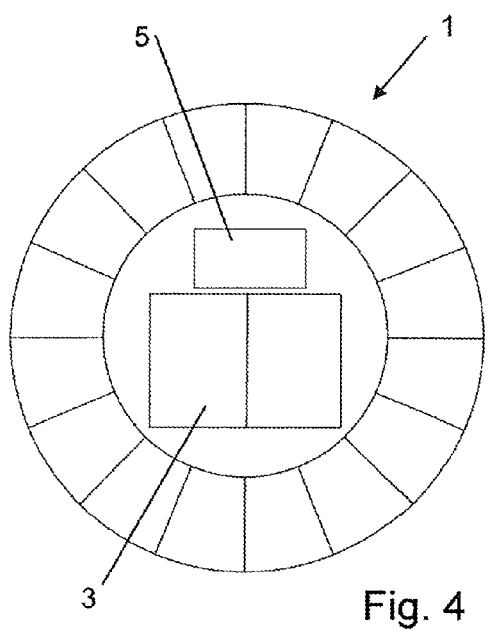
FIG. 4 a view of the distal end face of an applicator head.

FIG. 4 depicts a close-up of a central portion of an alternative applicator head as seen from the front (from the distal direction). In the configuration of FIG. 4, the UVA LEDs together have a more elongate rectangular shape compared to the versions of the previous figures; such an elongate shape can for example be present if the LEDs comprise for a 2×1 array if LEDs as schematically illustrated by the separation line. The shape of the LED(s) brings about a certain inhomogeneity. However, this has proven to be insubstantial if not negligible, and a homogenizing optics in front of the LED(s) is therefore optional and often not required.

The surface area of the portion (within the inner circle in FIG. 4) that comes into contact with the cornea is comparably small; in the depicted embodiment it is a fraction of the distal end surface portion having a diameter of 7 mm.

The number, geometry and arrangement of the LED(s) of the radiation source is generally not a critical issue. Rather, the number and arrangement of the LED(s) may be adapted to the chosen power requirements and the output power of the individual LED chips. It has been observed that small inhomogeneities of irradiation, which necessarily arise because of the characteristics of LEDs, are not critical for the treatment/prevention to be effective and also do not constitute any hazard.

Figure 5:
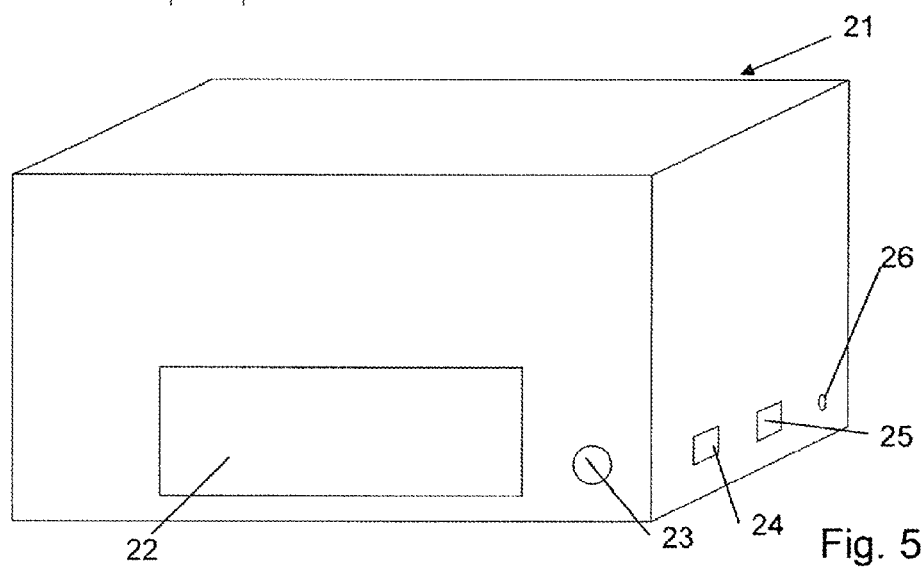
FIG. 5 a schematical view of a control unit.

FIG. 5 yet schematically depicts an electronic control unit 21 for being connected to the applicator head. The control unit 21 in the depicted configuration comprises an optional LCD screen 22 for displaying information to the ophthalmologist. In the shown embodiment, the electronic control unit in addition has a control light (visible LED) 23, an applicator head connector 24, a computer connector 25, and a power supply connector 26. The electronic control unit 21 may be connected to any suitable power source, including a battery unit (which, in contrast to the depicted configuration, may be integrated in a control unit housing), a DC power supply, system AC voltage, etc.

In alternative embodiments, the electronic control may be fully integrated into the applicator head, which then for example comprises a connector/connectors for being directly connectable to a power supply and/or a computer. The skilled person will realize that a separate power supply is not a necessity, as power can also be supplied via an appropriate interface directly from a computer or other central control unit, such as via a USB interface.

Figure 6:
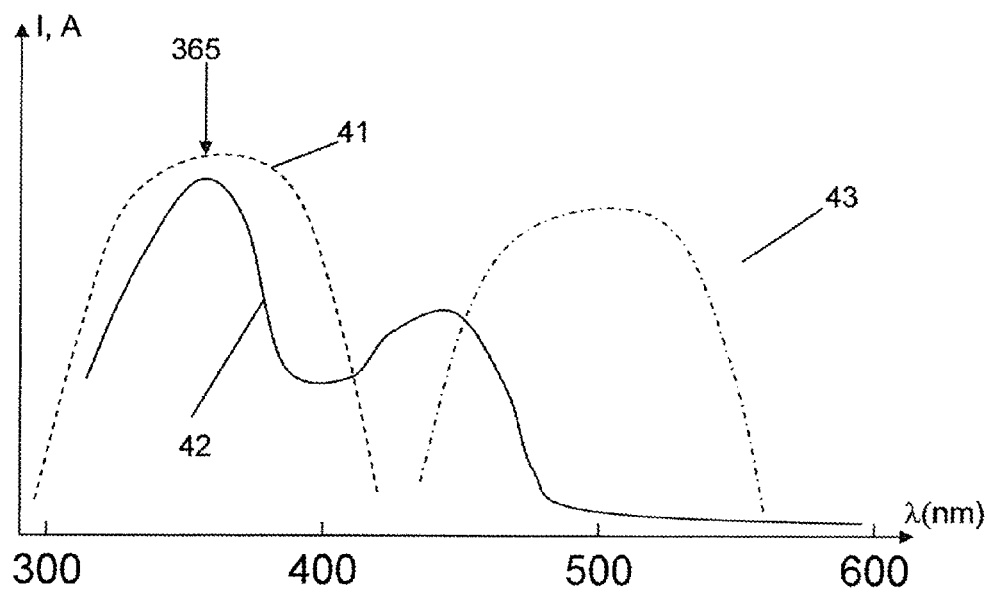
FIG. 6 a graph showing intensity and the absorption spectrum of a photoactivatable therapeutic agent (riboflavin taken as an example), as well as the emission spectrum of this agent and the emission spectrum of the LED.

The emission spectrum of the radiation source (the UVA LED(s) in the hereinbefore described embodiments) is adapted to the absorption spectrum of the chromophore of the phototherapeutic agent. This is very schematically illustrated in FIG. 6, where a first curve 41 schematically shows an emission spectrum of a 365 nm LED (thus an LED the emission spectrum of which has a single peak at 365 nm) and a second curve 42 illustrates the low energy part of the absorption spectrum of Riboflavin. The third curve shows an example of the sensitivity of the photodiode—the sensitivity should have only minimal overlap (if any) with the emission spectrum of the radiation source. It coincides well with the Riboflavin fluorescence emission spectrum. Generally, the sensitivity of the sensor can be influenced by the choice of the photodiode (or other device), and in addition optionally by an appropriate filter, for example a UV and/or blue filter.

Radiation at wavelengths below 300 nm, especially below about 280 nm, tends to be absorbed by DNA, and hence such short wavelength radiation should be avoided. In addition to the minimal overlap with the sensitivity of the photodiode that sets an upper limit of the wavelength, by this condition a lower limit of the wavelength is defined. Within the range defined by these two conditions, the radiation should have a high power spectral density at wavelengths where absorption by the chromophore is high.

Figure 7:
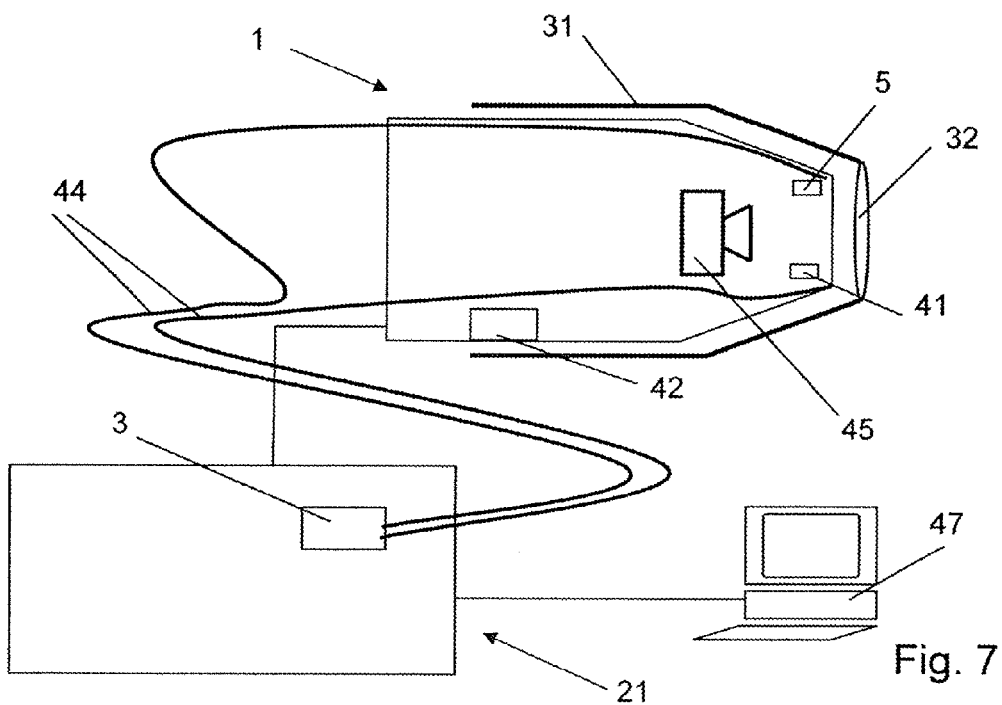
FIG. 7 a schematics of a further embodiment of an apparatus according to the invention.

FIG. 7 yet depicts another embodiment of an apparatus according to the invention. In contrast to the previously described embodiments, the applicator head 1 does not itself contain the UVA LED 3 as radiation emitting elements but the radiation sources are constituted by at least one (two in the shown configuration) fiber optic cable 44 the endings of which are at or near the distal end of the applicator head. The fiber optic cables 44 guide radiation emitted by the at least one radiation emitting element 3 to the applicator head and direct it onto the cornea when the applicator head is placed. The radiation emitting element(s) may especially be arranged in the control unit 21.

The embodiment of FIG. 7 further shows a disposable outer cover 31 (or 'single use tip') that can be attached to the applicator head casing to protect the cornea from non-sterile components. The outer cover 31 is transparent for visible and near-UV radiation at least in the region towards the distal end and in the depicted embodiment comprises an optional passive optical component in the form of a lens 32.

Within the housing the applicator comprises the sensor 5 for the fluorescent radiation. In the embodiment of FIG. 7, this sensor 5 does not serve as the first sensor that is used to detect proximity to the cornea. Rather, a separate, independent proximity sensor 41, for example an IR or ultrasound proximity sensor is present in the applicator head in addition to the fluorescent sensor 5. Further, the applicator head 1 comprises a barcode reader 42 (or similar) to capture a sign carried (visibly or non-visibly) by the applicator head that identifies the applicator head to make sure that the same outer cover 31 cannot be used in two treatments.

The applicator head 1 in the depicted embodiment further comprises a camera 45 that is placed to capture images (continuously or triggered by certain events) of the cornea.

In FIG. 7, the connections between the control unit 21 and the applicator head 1 as well as between the control unit 21 and a computer 47 are depicted only schematically; the skilled person will realize that the connector for a plug-and-socket connection may include electrical or possibly optical connections for both, power supply and control of the components in the applicator head as well as for the data transmission from the camera and/or other sensors to the control and ultimately (if present) to the computer 47.

Various other embodiments are possible. For example, it would be possible to have the sensing element for the fluorescence sensor 5 or (depending on the technology) even the proximity sensor 41 placed in the control unit and connected to the applicator head by fiber optics or, for example in the case of a capacitance sensor, by an electrical connection. It is even possible to configure the apparatus so that the applicator head does not have any active components at all but that the radiation source as well as the sensor(s) are constituted by ends of fiber optic cables or electrodes or similar connected to active devices (radiation emitting element; radiation sensor, capacitance sensor etc.) placed remotely, especially in the control unit.

What is claimed is:

1. An apparatus for the treatment and/or prevention of corneal diseases, the apparatus comprising:
    an applicator head, the applicator head comprising a radiation source configured to emit a first radiation capable of exciting a non-toxic therapeutic substance applied to a cornea; and
    a control operable to activate the radiation source to radiate the first radiation;
    wherein the applicator head further comprises a fluorescence sensor configured to obtain a measurement result by measuring a fluorescent radiation emitted by the non-toxic therapeutic substance upon irradiation by the first radiation, the fluorescent radiation having a spectral composition different from a spectral composition of the first radiation,
    wherein the control is configured to use the measurement result from the fluorescence sensor:
        to evaluate whether the applicator head is within a predetermined distance from the cornea,
        to evaluate whether a predetermined amount of the non-toxic therapeutic substance is present on the cornea, and
        to activate the radiation source to further radiate only when the measurement result indicates that the applicator head is within the predetermined distance from the cornea and that the predetermined amount of the non-toxic therapeutic substance is present on the cornea.

2. The apparatus according to claim 1, the applicator head further comprising a proximity sensor sensing whether the applicator head makes contact with the cornea.

3. The apparatus according to claim 1, wherein the applicator head is equipped for enabling a visual control of a physical contact between the applicator head and the cornea.

4. The apparatus according to claim 1, wherein the applicator head is configured to be a single-use component.

5. The apparatus according to claim 1, wherein the applicator head comprises a connector for a plug-and socket connection to a control unit, a computer and/or a power source.

6. The apparatus according claim 1, wherein the radiation source comprises or is connected to a single LED or a plurality of LEDs as radiation generating means.

7. The apparatus according to claim 1, wherein the radiation source is configured to radiate at powers between 0.5 mW and 25 mW.

8. The apparatus according to claim 1, wherein the radiation source comprises at least one fiber optic cable that connects a distal portion of the applicator head with a radiation generating element placed outside of the applicator head.

9. The apparatus according to claim 1, wherein the applicator head further comprises a camera placed to monitor the cornea during treatment.

10. The apparatus according to claim 1, further comprising an at least partially transparent, exchangeable outer cover shaped to be placed to partially encase an applicator head housing.

11. The apparatus according to claim 10, further comprises an optical lens.

12. The apparatus according to claim 1, wherein the applicator head is shaped to cooperate with a mount of a standard Goldmann applanation tonometer used in slit lamps.

13. The apparatus according to claim 12, wherein the applicator head has a housing with a cylindrical proximal portion.

14. The apparatus according to claim 1, wherein the radiation emitted by the radiation source is radiation with a specific wavelength between 280 and 1300 nm, dependent on an absorption spectrum of a photoactive therapeutic agent being the non-toxic therapeutic substance.

15. The apparatus according to claim 14, wherein the apparatus is configured to excite Riboflavin as the non-toxic therapeutic substance and wherein the emission spectrum of the radiation source has a substantial power spectral density at 365 nm wavelength.

16. An applicator head for an apparatus for the treatment and/or prevention of corneal diseases, the applicator head comprising:
a radiation source capable of emitting a first radiation that excites a non-toxic therapeutic substance applied to a cornea;
a fluorescence sensor configured to obtain a measurement result by measuring a fluorescent radiation emitted by the non-toxic therapeutic substance upon irradiation by the first radiation, the fluorescent radiation having a spectral composition different from a spectral composition of the first radiation; and
a control or a connector to a control;
wherein the control is configured to use the measurement result from the fluorescence sensor:
to evaluate whether the applicator head is within a predetermined distance from the cornea,
to evaluate whether a predetermined amount of the non-toxic therapeutic substance is present on the cornea, and
to activate the radiation source to further radiate only when the measurement result indicates that the applicator head is within the predetermined distance from the cornea and that the predetermined amount of the non-toxic therapeutic substance is present on the cornea.

17. A kit of parts comprising an applicator head according to claim 16, further comprising a dose of a photoactive therapeutic agent as the non-toxic therapeutic substance.

18. A control unit of an apparatus for the treatment and/or prevention of corneal diseases, the control unit comprising an interface to an applicator head,
a radiation source configured to emit a first radiation, and
a fluorescence sensor configured to obtain a measurement result by measuring a fluorescent radiation emitted, upon irradiation by the first radiation, by a non-toxic therapeutic substance applied to the cornea, the fluorescent radiation having a spectral composition different from a spectral composition of the first radiation,
wherein the control unit is configured to use the measurement result from the fluorescence sensor:
to evaluate whether the applicator head is within a predetermined distance from the cornea;
to evaluate whether a predetermined amount of the non-toxic therapeutic substance is present on the cornea, and
to activate the radiation source to further radiate only when the measurement result indicates that the applicator head is within the predetermined distance from the cornea and that the predetermined amount of the non-toxic therapeutic substance is present on the cornea.

19. A method of treating and/or preventing a corneal disease, the method comprising the steps of:
applying a therapeutic amount of a photoactive therapeutic agent to a cornea;
providing an apparatus with an applicator head, the applicator head comprising a radiation source configured to emit a first radiation capable of exciting a chromophore of the photoactive therapeutic agent and activating the photoactive therapeutic agent;
positioning the applicator head near the cornea;
obtaining a measurement result by measuring, with a fluorescence sensor, a fluorescent radiation of a spectral composition different from a spectral composition of the first radiation, the fluorescent radiation emitted by the chromophore upon irradiation by the first radiation,
using the measurement result from the fluorescence sensor to evaluate whether a condition is met that:
the applicator head is within a predetermined distance from the cornea, and
a predetermined amount of the chromophore is present on the cornea; and
in case the condition is met, further irradiating the cornea by the radiation source and thereby activating the photoactive therapeutic agent.

* * * * *